United States Patent
McCabe

(10) Patent No.: US 7,374,627 B2
(45) Date of Patent: May 20, 2008

(54) METHOD OF PRODUCING AN ULTRASONICALLY BONDED LAP SEAM

(75) Inventor: John A. McCabe, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 377 days.

(21) Appl. No.: 11/100,895

(22) Filed: Apr. 7, 2005

(65) Prior Publication Data

US 2005/0230024 A1    Oct. 20, 2005

Related U.S. Application Data

(60) Provisional application No. 60/563,518, filed on Apr. 19, 2004.

(51) Int. Cl.
*B32B 37/00*    (2006.01)

(52) U.S. Cl. .............. 156/73.1; 156/290; 156/308.4

(58) Field of Classification Search .............. 156/73.1, 156/73.4, 91, 92, 93, 157, 159, 290, 304.1, 156/304.3, 308.4
See application file for complete search history.

(56) References Cited

U.S. PATENT DOCUMENTS

| | | | |
|---|---|---|---|
| 135,145 A | 1/1873 | Murphy | |
| 293,353 A | 2/1884 | Purvis | |
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,605,842 A | 11/1926 | Jones | |
| 1,957,651 A | 5/1934 | Joa | |
| 2,009,857 A | 7/1935 | Potdevin | |
| 2,054,832 A | 9/1936 | Potdevin | |
| 2,128,746 A | 8/1938 | Joa | |
| 2,131,808 A | 10/1938 | Joa | |
| 2,164,408 A | 7/1939 | Joa | |
| 2,167,179 A | 7/1939 | Joa | |
| 2,171,741 A | 9/1939 | Cohn et al. | |
| 2,213,431 A | 9/1940 | Joa | |
| 2,254,290 A | 9/1941 | Joa | |
| 2,254,291 A | 9/1941 | Joa | |
| 2,282,477 A | 5/1942 | Joa | |
| 2,286,096 A | 6/1942 | Joa | |
| 2,296,931 A | 9/1942 | Joa | |

(Continued)

FOREIGN PATENT DOCUMENTS

CA    1146129    5/1983

(Continued)

OTHER PUBLICATIONS

Reciprocating Mechanisms, Ingenious Mechanisms for Designers and Inventors, Franklin Jones vol. 1.

*Primary Examiner*—James Sells
(74) *Attorney, Agent, or Firm*—Ryan, Kromholz & Manion S.C.

(57) ABSTRACT

A method of forming a lap seam for a disposable undergarment is disclosed. The method involves the steps of providing a continuous web of material, folding the material, cutting the material into individual undergarment blanks, folding the edges of the individual blanks, and sealing the edges. The method preferably employs undergarment blanks that are asymmetrical in shape.

11 Claims, 4 Drawing Sheets

U.S. PATENT DOCUMENTS

| | | |
|---|---|---|
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,772,120 A | 11/1973 | Radzins |
| 3,796,360 A | 3/1974 | Alexeff |
| 3,816,210 A | 6/1974 | Aoko et al. |
| 3,854,917 A | 12/1974 | McKinney et al. |
| 3,883,389 A | 5/1975 | Schott, Jr. |
| 3,888,400 A | 6/1975 | Wiig |
| 3,904,147 A | 9/1975 | Taitel et al. |
| 3,918,698 A | 11/1975 | Coast |
| 3,960,646 A | 6/1976 | Wiedamann |
| 3,991,994 A | 11/1976 | Farish |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,094,319 A | 6/1978 | Joa |
| 4,106,974 A | 8/1978 | Hirsch |
| 4,108,584 A | 8/1978 | Radzins et al. |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,215,827 A | 8/1980 | Roberts et al. |
| 4,222,533 A | 9/1980 | Pongracz |
| 4,223,822 A | 9/1980 | Clitheroe |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,342,206 A | 8/1982 | Rommel |
| 4,364,787 A | 12/1982 | Radzins |
| 4,374,576 A | 2/1983 | Ryan |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisnecki et al. |
| 4,701,239 A | 10/1987 | Craig |
| 4,726,874 A | 2/1988 | VanVliet |
| 4,726,876 A | 2/1988 | Tomsovic et al. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,795,510 A | 1/1989 | Wittrock et al. |
| 4,801,345 A | 1/1989 | Dussaud et al. |
| 4,802,570 A | 2/1989 | Hirsch et al. |
| 4,840,609 A | 6/1989 | Jones et al. |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,925,520 A | 5/1990 | Beaudoin et al. |
| 4,927,322 A | 5/1990 | Schweizer et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |

| | | | | | | |
|---|---|---|---|---|---|---|
| 4,994,010 A | 2/1991 | Doderer-Winkler | | 6,079,343 A * | 6/2000 | Wong .................... 112/475.09 |
| 5,000,806 A | 3/1991 | Merkatoris et al. | | 6,098,249 A | 8/2000 | Toney et al. |
| 5,021,111 A | 6/1991 | Swenson | | 6,123,792 A | 9/2000 | Samida et al. |
| 5,025,910 A | 6/1991 | Lasure et al. | | 6,183,576 B1 | 2/2001 | Couillard et al. |
| 5,045,039 A | 9/1991 | Bay | | 6,210,386 B1 | 4/2001 | Inoue |
| 5,080,741 A | 1/1992 | Nomura et al. | | 6,264,784 B1 | 7/2001 | Menard et al. |
| 5,094,658 A | 3/1992 | Smithe et al. | | 6,306,122 B1 | 10/2001 | Narawa et al. |
| 5,096,532 A | 3/1992 | Neuwirth et al. | | 6,309,336 B1 | 10/2001 | Muessig et al. |
| 5,108,017 A | 4/1992 | Adamski et al. | | 6,312,420 B1 | 11/2001 | Sasaki et al. |
| 5,109,767 A | 5/1992 | Nyfeler et al. | | 6,314,333 B1 | 11/2001 | Rajala et al. |
| 5,110,403 A | 5/1992 | Ehlert | | 6,315,022 B1 | 11/2001 | Herrin et al. |
| 5,127,981 A | 7/1992 | Straub et al. | | 6,336,921 B1 | 1/2002 | Kato et al. |
| 5,131,525 A | 7/1992 | Musschoot | | 6,358,350 B1 | 3/2002 | Glaug et al. |
| 5,147,487 A | 9/1992 | Nomura et al. | | 6,369,291 B1 | 4/2002 | Uchimoto et al. |
| 5,163,594 A | 11/1992 | Meyer | | 6,375,769 B1 | 4/2002 | Quereshi et al. |
| 5,171,239 A | 12/1992 | Igaue et al. | | 6,391,013 B1 | 5/2002 | Suzuki et al. |
| 5,176,244 A | 1/1993 | Radzins et al. | | 6,416,697 B1 | 7/2002 | Venturino et al. |
| 5,183,252 A | 2/1993 | Wolber et al. | | 6,473,669 B2 | 10/2002 | Rajala et al. |
| 5,188,627 A | 2/1993 | Igaue et al. | | 6,475,325 B1 | 11/2002 | Parrish et al. |
| 5,195,684 A | 3/1993 | Radzins | | 6,478,786 B1 | 11/2002 | Gloug et al. |
| 5,213,645 A | 5/1993 | Nomura et al. | | 6,482,278 B1 | 11/2002 | McCabe et al. |
| 5,223,069 A | 6/1993 | Tokuno et al. | | 6,494,244 B2 | 12/2002 | Parrish et al. |
| 5,226,992 A | 7/1993 | Morman | | 6,521,320 B2 * | 2/2003 | McCabe et al. ............ 428/137 |
| 5,246,433 A | 9/1993 | Hasse et al. | | 6,524,423 B1 | 2/2003 | Hilt et al. |
| 5,267,933 A | 12/1993 | Precoma | | 6,551,228 B1 | 4/2003 | Richards |
| 5,308,345 A | 5/1994 | Herrin | | 6,551,430 B1 | 4/2003 | Glaug et al. |
| 5,340,424 A | 8/1994 | Matsushita | | 6,554,815 B1 | 4/2003 | Umebayashi |
| 5,407,513 A | 4/1995 | Hayden et al. | | 6,572,520 B2 | 6/2003 | Blumle |
| 5,415,649 A | 5/1995 | Watanabe et al. | | 6,596,108 B2 | 7/2003 | McCabe |
| 5,421,924 A | 6/1995 | Ziegelhoffer et al. | | 6,605,172 B1 | 8/2003 | Anderson et al. |
| 5,424,025 A | 6/1995 | Hanschen et al. | | 6,605,173 B2 | 8/2003 | Glaug et al. |
| 5,435,802 A | 7/1995 | Kober | | 6,648,122 B1 | 11/2003 | Hirsch et al. |
| 5,449,353 A | 9/1995 | Watanabe et al. | | 6,649,010 B2 | 11/2003 | Parrish et al. |
| 5,464,401 A | 11/1995 | Hasse et al. | | 6,659,991 B2 | 12/2003 | Suekane |
| 5,494,622 A | 2/1996 | Heath et al. | | D497,991 S | 11/2004 | Otsubo et al. |
| 5,540,647 A | 7/1996 | Weiermann et al. | | 6,820,671 B2 | 11/2004 | Calvert |
| 5,545,275 A | 8/1996 | Herrin et al. | | 6,837,840 B2 | 1/2005 | Yonekawa et al. |
| 5,545,285 A | 8/1996 | Johnson | | 6,840,616 B2 | 1/2005 | Summers |
| 5,552,013 A | 9/1996 | Ehlert et al. | | 6,875,202 B2 | 4/2005 | Kumasaka et al. |
| 5,556,360 A | 9/1996 | Kober et al. | | 7,077,393 B2 | 7/2006 | Ishida |
| 5,556,504 A | 9/1996 | Rajala et al. | | 7,172,666 B2 | 2/2007 | Groves et al. |
| 5,560,793 A | 10/1996 | Ruscher et al. | | 7,214,174 B2 | 5/2007 | Allen et al. |
| 5,602,747 A | 2/1997 | Rajala | | 2001/0012813 A1 | 8/2001 | Bluemle |
| 5,624,420 A | 4/1997 | Bridges et al. | | 2001/0017181 A1 | 8/2001 | Otruba et al. |
| 5,628,738 A | 5/1997 | Suekane | | 2002/0046802 A1 | 4/2002 | Tachibana et al. |
| 5,634,917 A | 6/1997 | Fujioka et al. | | 2002/0059013 A1 | 5/2002 | Rajala et al. |
| 5,643,165 A | 7/1997 | Klekamp | | 2003/0000620 A1 | 1/2003 | Herrin et al. |
| 5,643,396 A | 7/1997 | Rajala et al. | | 2003/0052148 A1 | 3/2003 | Rajala et al. |
| 5,645,543 A | 7/1997 | Nomura et al. | | 2003/0066585 A1 | 4/2003 | McCabe |
| 5,659,229 A | 8/1997 | Rajala | | 2003/0083638 A1 | 5/2003 | Malee |
| 5,660,657 A | 8/1997 | Rajala et al. | | 2003/0084984 A1 | 5/2003 | Glaug et al. |
| 5,660,665 A | 8/1997 | Jalonen | | 2003/0089447 A1 | 5/2003 | Molee et al. |
| 5,683,376 A | 11/1997 | Kato et al. | | 2003/0135189 A1 | 7/2003 | Umebayashi |
| RE35,687 E | 12/1997 | Igaue et al. | | 2004/0016500 A1 | 1/2004 | Tachibana et al. |
| 5,693,165 A | 12/1997 | Schmitz | | 2005/0000628 A1 | 1/2005 | Norrley |
| 5,707,470 A | 1/1998 | Rajala et al. | | 2005/0230056 A1 | 10/2005 | Meyer et al. |
| 5,711,832 A | 1/1998 | Glaug et al. | | 2005/0230449 A1 | 10/2005 | Meyer et al. |
| 5,745,922 A | 5/1998 | Rajala et al. | | 2005/0233881 A1 | 10/2005 | Meyer |
| 5,746,869 A | 5/1998 | Hayden et al. | | 2005/0234412 A1 | 10/2005 | Andrews et al. |
| 5,749,989 A | 5/1998 | Linman et al. | | 2005/0257881 A1 | 11/2005 | Coose et al. |
| 5,788,797 A | 8/1998 | Herrin et al. | | 2005/0275148 A1 | 12/2005 | Beaudoin et al. |
| 5,817,199 A | 10/1998 | Brennecke et al. | | 2006/0224137 A1 | 10/2006 | McCabe et al. |
| 5,836,931 A | 11/1998 | Toyoda et al. | | 2006/0265867 A1 | 11/2006 | Schaap |
| 5,858,012 A | 1/1999 | Yamaki et al. | | 2007/0074953 A1 | 4/2007 | McCabe |
| 5,865,393 A | 2/1999 | Kreft et al. | | | | |
| 5,868,727 A | 2/1999 | Barr et al. | | FOREIGN PATENT DOCUMENTS | | |
| 5,876,027 A | 3/1999 | Fukui et al. | | | | |
| 5,879,500 A | 3/1999 | Herrin et al. | | CA | 1153345 | 9/1983 |
| 5,932,039 A | 8/1999 | Popp et al. | | CA | 1190078 | 7/1985 |
| 5,964,970 A | 10/1999 | Woolwine et al. | | CA | 1210744 | 9/1986 |
| 6,036,805 A | 3/2000 | McNichols | | CA | 1212132 | 9/1986 |
| 6,050,517 A | 4/2000 | Dobrescu et al. | | CA | 1236056 | 5/1988 |
| 6,074,110 A | 6/2000 | Verlinden et al. | | CA | 1249102 | 1/1989 |

| | | | | | |
|---|---|---|---|---|---|
| CA | 1292201 | 11/1991 | ES | 520559 | 12/1983 |
| CA | 1307244 | 9/1992 | ES | 296211 | 12/1987 |
| CA | 1308015 | 9/1992 | FR | 2891811 | 4/2007 |
| CA | 1310342 | 11/1992 | GB | 191101501 | 1/1912 |
| CA | 2023816 | 3/1994 | GB | 439897 | 12/1935 |
| CA | 2404154 | 10/2001 | JP | 428364 | 1/1992 |
| CA | 2541194 | 1/2006 | JP | 542180 | 2/1993 |
| CA | 2559517 | 5/2007 | JP | 576566 | 3/1993 |
| DE | 102006047280 | 4/2007 | JP | 626160 | 2/1994 |
| EP | 0048011 | 3/1982 | JP | 626161 | 2/1994 |
| EP | 0089106 | 9/1983 | JP | 6197925 | 7/1994 |
| EP | 0304140 | 8/1987 | JP | 10-277091 | 10/1998 |
| EP | 0439897 | 2/1990 | SE | 0602047 | 5/2007 |
| EP | 0455231 | 11/1991 | WO | WO9907319 | 2/1999 |
| EP | 510251 | 10/1992 | WO | WO9913813 | 3/1999 |
| EP | 0652175 | 5/1995 | WO | WO9965437 | 12/1999 |
| EP | 0901780 | 3/1999 | WO | WO0143682 | 6/2001 |
| EP | 1132325 | 9/2001 | WO | WO0172237 | 10/2001 |
| EP | 1272347 | 1/2003 | WO | WO2005075163 | 1/2005 |
| EP | 1707168 | 4/2006 | | | |
| ES | 509706 | 11/1982 | | | |

* cited by examiner

METHOD OF PRODUCING AN ULTRASONICALLY BONDED LAP SEAM

RELATED APPLICATION

This application claims the benefit of U.S. Provisional Patent Application Ser. No. 60/563,518, filed 19 Apr. 2004, and entitled "Method of Producing an Ultrasonically Bonded Lap Seam."

BACKGROUND OF THE INVENTION

The invention relates to disposable garments, and more particularly, a pants-type diaper, and methods of producing such garments. Disposable diapers of the children's training pant type, or of the adult incontinence type, have generally been made with a standard fashion. The disposable garments are typically produced in a laid-flat blank format, with the blanks forming a continuous web of material. The final form of the diaper is achieved by folding the blanks in half, either before or after they are cut from the web of material. The blanks must also be sealed along the side edges to form the final diaper shape.

With such transversely produced products, the side seals or bonds are created in the form of a cross-directional weld, typically produced either ultrasonically or thermally. When the folded flats are run through a bonding unit, either before or after the flats are cut into individual flats, the edges are held out so that all layers of the web are welded together. This results in the formation of a butt seam or weld.

Butt seams are inherently weak because normal usage applies forces, called peel forces, to the bond, which are relatively damaging to the bond. Such forces focus along the leading edges of the bond formation and push outwardly from the bond seam. When the flats are welded together, the bonding process essentially is a destructive process. The small welded area is subject to a large peel force that tends to push apart the bonded edges. Thus, a more durable bonding process is desirable.

A more suitable and durable type of seam would be a lap seam. Typically overlaying or layering the edges of the materials to be bonded forms a lap seam, which subjects the garment edges to shear forces as opposed to peel forces. Such a design is advantageous because the forces are typically distributed over the entire bonded area as opposed to the edges of the bond. However, lap seams have not been previously used, as it is difficult in positioning an anvil and a sealing machine used in the bonding process in a manner that would allow formation of a lap seam.

SUMMARY OF THE INVENTION

The current invention is a method for producing a disposable undergarment, with the lateral edges of the undergarment bonded by means of a lap seam instead of a butt seam. When a blank is formed for an individual undergarment, the lateral edges of opposing halves of the blank will form the lap seam. After the blank is folded along a central axis, one of the lateral edges of the first half of the blank is folded over and around the lateral edge of the opposing second half of the blank. When the edges are sealed together, a lap seam is formed.

While such an arrangement is possible with known symmetrical blank configurations, using an asymmetrical blank may efficiently form the seam. The lateral edges of the opposite halves do not align when the blank is folded along the central axis. The edge to be folded extends farther from the middle of the blank than the opposing edge. The folded edge may then be easily manipulated without interference from the opposing edge, which allows a smooth transition to a bonding unit.

The lap seam is not formed directly to the overlaying lateral edges. The side panels are composed of a material that is not thermally or ultrasonically bondable. Before the blank passes through a bonding unit, a polymer substrate is placed between the side panels. The polymer acts as an interface, attaching itself to both surfaces. A resulting bond is formed between the two surfaces.

The method generally consists of the steps of providing a continuous web of material to form a disposable undergarment, cutting the material into individual undergarment blanks, folding the blanks along a central axis, folding the blanks along the edges in an overlapping fashion to form a lap seam, and sealing the edges to form individual garments.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention.

Figure 1:
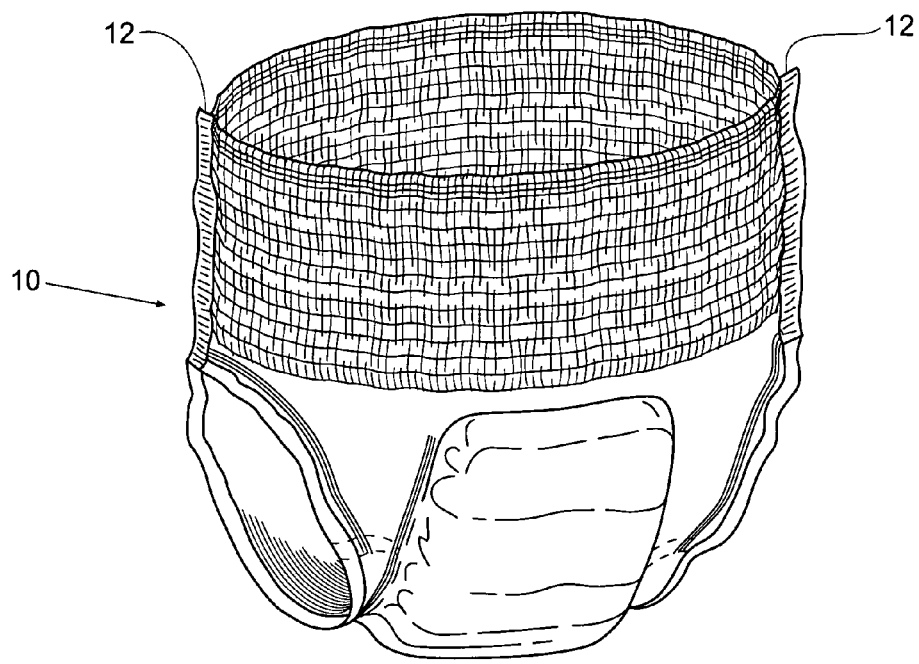
FIG. 1 shows a seam for a disposable undergarment as formed by the prior art.

FIG. 1 shows a perspective view of a disposable undergarment 10 formed according to the prior art. A pair of end welds or seams 12 allows the undergarment 10 to be formed from a laid-flat blank (not shown). The seams 12 are formed using a standard process, such as an ultrasonic or thermal process, wherein opposing ends of the blank are sealed together to form the seams 12. These seams are commonly referred to as butt seams. An inherent problem for butt seams is the tendency for the seams to break apart when normal forces or peel forces associated with wearing the undergarments are applied to the undergarments. Since such peel forces are focused along the leading edges of the butt seam 12, the seams will slowly be peeled apart and eventually may lead to the seams splitting.

The present invention reduces peel forces by introducing a lap seam in place of the butt seam. Typically, a lap seam is produced by overlaying one web over another. The overlay is then placed between a bonder and an anvil to form the lap seam. However, it is often difficult to get the overlayed webs between the bonder and the anvil to form the desired seam.

Figure 2A:
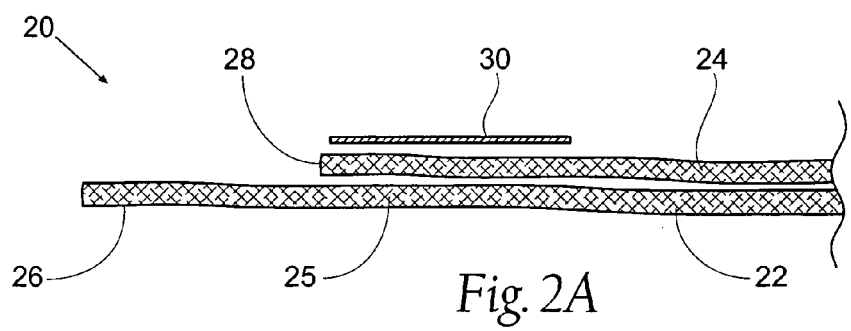
FIG. 2A is an exploded cross-sectional view of the materials to be bonded according to the present invention.
Figure 2B:
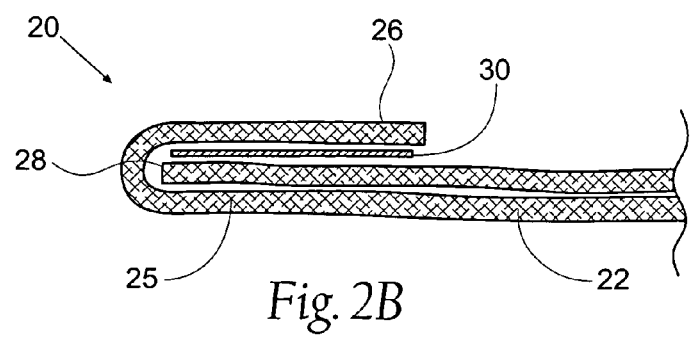
FIG. 2B shows an exploded cross-sectional view of a seam for a disposable undergarment as produced by the current method.

FIGS. 2A and 2B show exploded cross-sectional views of a seam 20 being formed according to the current method to replace the butt seam 12 of the prior art (see FIG. 1). The seam 20, referred to as a lap seam, allows a disposable undergarment to be subject to shear forces instead of peel forces. Such forces are preferred over peel forces since the shear forces are typically distributed over all areas of the seam, which enhances the total strength of the bond.

Referring specifically to FIG. 2A, a first web 22 and a second web 24 are shown. The webs 22 and 24 are selected to be of such a nature as to not be thermally or ultrasonically bondable. An example of such non-bondable material would be a paper-based carded nonwoven material. The second web 24 is placed atop of a section 25 of the first web 22. An end 26 of the first web 22 extends past an end 28 of the second web 24. A polymer substrate 30 is placed atop of the second web 24. The polymer substrate 30 is aligned approximately near the edge of the second web end 28. An example of such a substrate would be the thermoplastic adhesive film #6218 supplied by Bemis Associates, Inc., of Shirley, Mass. Such similar adhesive films are commonly used for bonding medium density fiberboard PVC sheeting in the manufacture of kitchen cabinetry.

Referring to FIG. 2B, the first web end 26 is shown folded over the second web end 28. The polymer substrate 30 lies between the second web end 28 and the first web end 26, which are the areas that are to be bonded. The substrate 30 acts as an interface media between the two web ends 26 and 28, attaching itself to both surfaces, but not to the section 25 of the first web 22. Thus, a bond is formed between the first web end 26 and the second web end 28, but the section 25 of the first web 22 is left unbonded. The bonded materials now form a lap seam.

Figure 3:
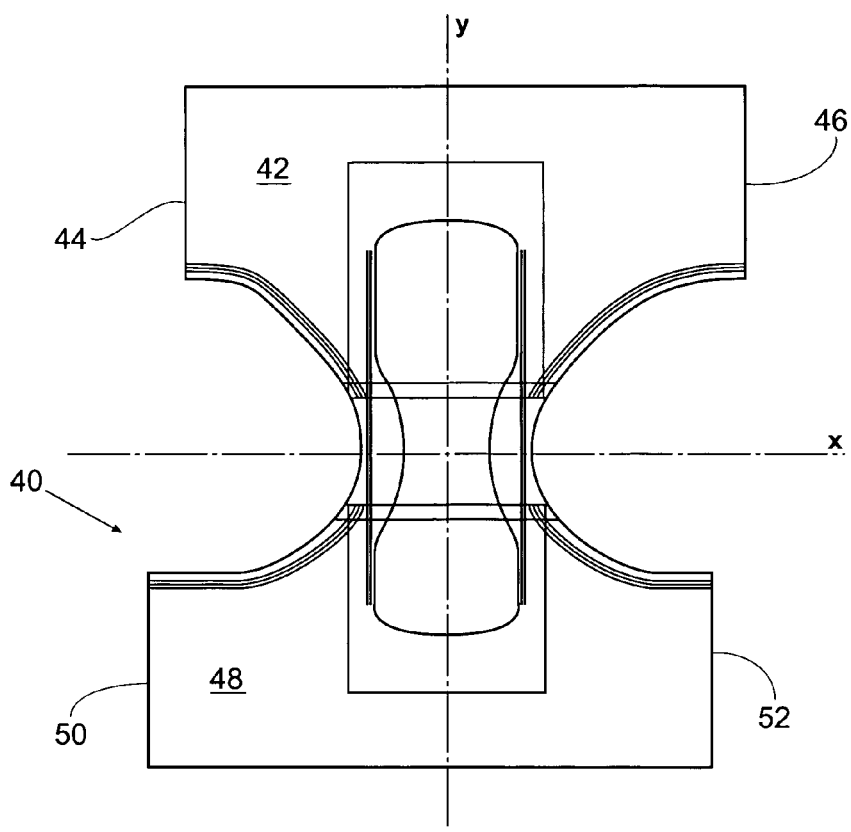
FIG. 3 represents an overhead view of an undergarment blank utilized in the present method.

One possibility of a blank used to form the lap seam 20 is shown in FIG. 3. The blank 40 has an altered shape from blanks that are common in the prior art. While most blanks are designed in a symmetrical fashion, the blank 40 is asymmetrical along both the X- and Y-axis. The blank is made up of a first half 42, having a first edge 44 and a second edge 46, and a second half 48 having a first edge 50 and a second edge 52. Though the blank 40 is not symmetrical, the first half 42 and the second half 48 are preferably the same shape and size just not aligned along the axes. That is, the area of the first half 42 and the second half 48 should be the same, just not aligned along the y-axis.

Figure 4:
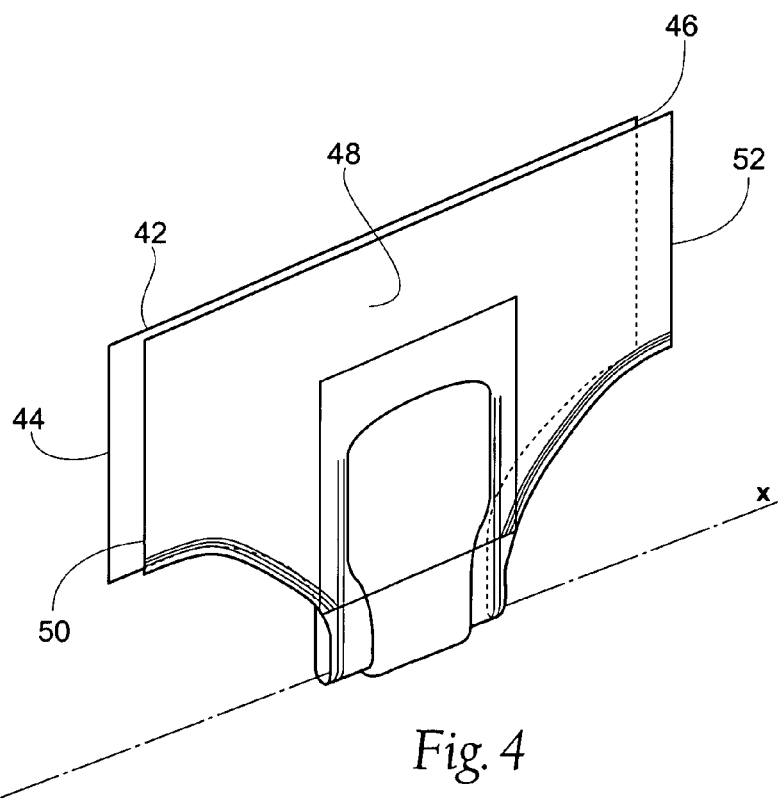
FIG. 4 is a perspective view of the blank shown in FIG. 3 folded along an axis.

Normally, when an undergarment blank is folded along the X-axis, the edges of the blank halves will align. However, as shown in FIG. 4, folding the blank 40 along the X-axis does not align the edges. For instance, the first edge 44 of the first half 42 is not aligned with the first edge 50 of the second half 48, and the second edge 46 of the first half 44 is not aligned with the second edge 52 of the second half 48. Thus, the lap seam 20 described above and in FIGS. 2A and 2B may be formed, with the first edge 44 of the first half 42 folded over the first edge 50 of the second half 48, and the second edge 52 of the second half 48 folded over the second edge 46 of the first half 42. The edges are folded over without any undue manipulation of the blank.

Figure 5:
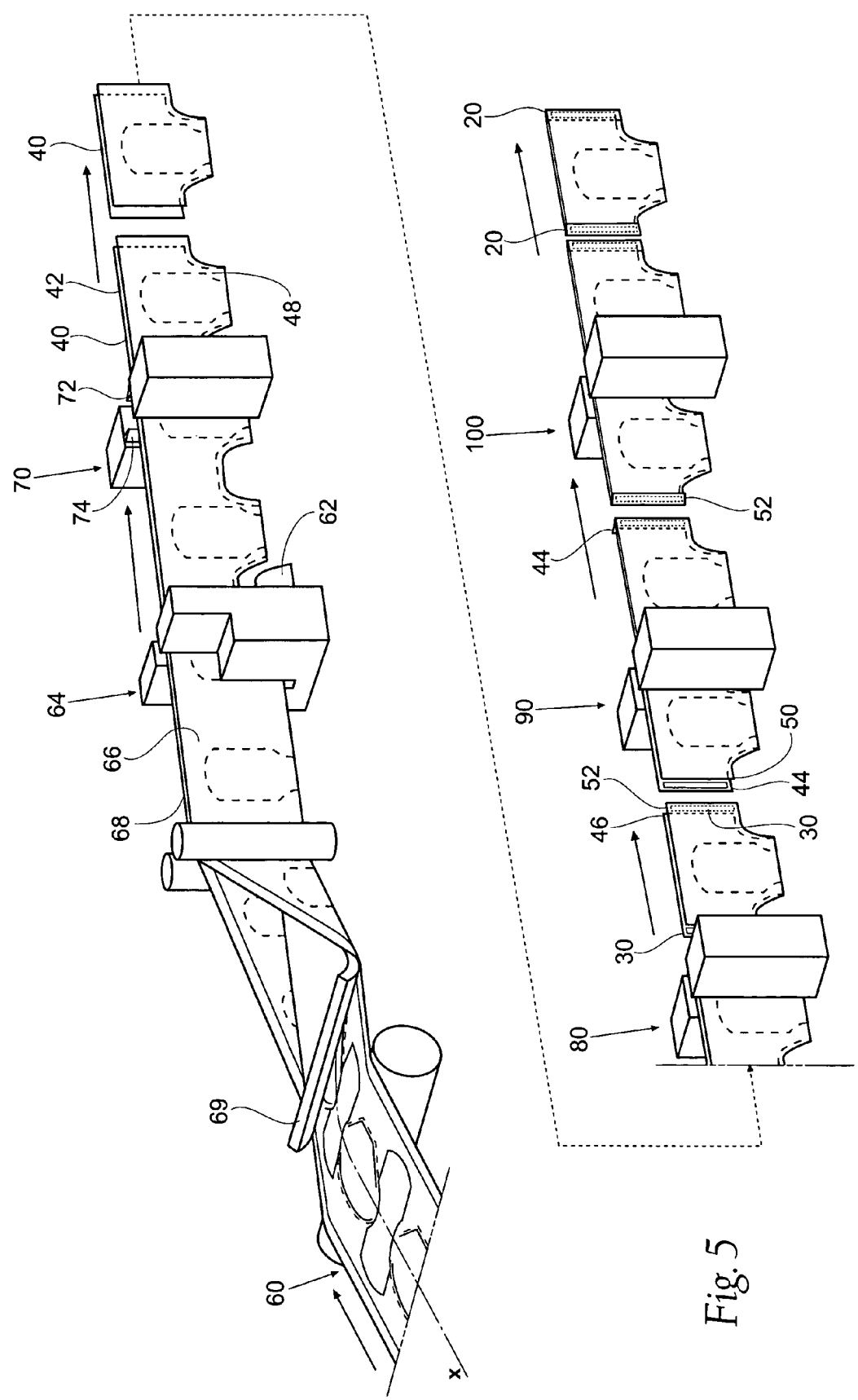
FIG. 5 is a schematic view of an undergarment being formed using the present invention.

FIG. 5 depicts a schematic representation of a process of making a disposable undergarment with a lap seam. A continuous web of material 60 is fed through a machine or system, as the schematic representation in FIG. 5 shows. Leg hole materials 62, if not previously removed, are cut at a cutting station 64, thereby removing the material 62. The continuous web of material 60 is folded, before or after cutting out the leg holes, longitudinally along the X-axis with a plow member 69 or other similar folding device. The folding process brings together a front waist edge 66 with a back waist edge 68. The continuous web 60 is then separated into separate blanks 40 by passing through a cut-off knife assembly 70, which severs the web 60 along the transverse axis of the eventual side seam welds. Because the blank is cut in asymmetrical fashion, the transverse axes associated with the first half 42 of the blank 40 will not align with the transverse axes of the second half 48 of the blank 40 after leaving the knife assembly 70. The cut-off knife assembly 70 may be arranged in such a fashion that a blade 72 of the knife assembly 70 for cutting the front waist edge 66 side seams is not aligned with a blade 74 of the knife assembly 70 for cutting the back waist edge 68 side seams. As a result, the asymmetrical blanks 40 shown and described in FIGS. 3 and 4 are formed.

Still referring to FIG. 5, once the individual blanks 40 are cut, they are fed through an adhering assembly 80, where the substrate 30 is placed along the blank edges 44 and 52 (see FIG. 4). The substrate 30 should be placed on the side of the edges 44 and 52 that will face the edges 50 and 46. A folding assembly 90 folds the edges 44 and 52 over the edges 50 and 46, respectively. FIG. 5 shows that the edges 44 and 52 are not parallel to the blank 40 after leaving the folding assembly 90. This is shown only as a visual aid to represent the folding process. Normally, the edges 44 and 52 will be folded flush with the blank 40. Once folded over, a sealing device 100 then welds the respective edges together, which results in the formation of lap seams 20. The folding assembly 90 results in a smooth transition to the sealing device 100, so that it will be easier to pass the blank 40 through the sealing device and form the lap seam 20.

Figure 6:
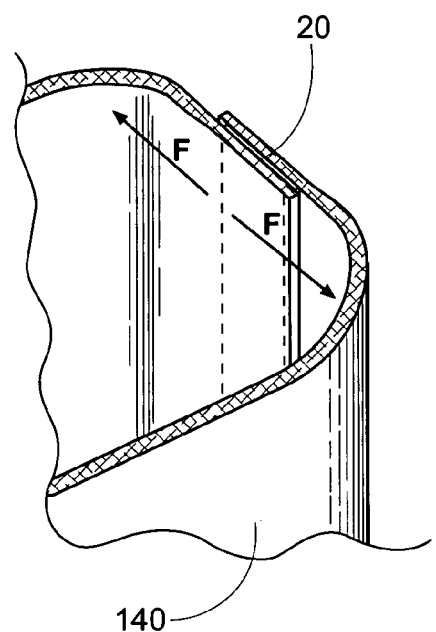
FIG. 6 shows an exploded sectional view of a lap seam formed according to the present invention.
Figure 7:
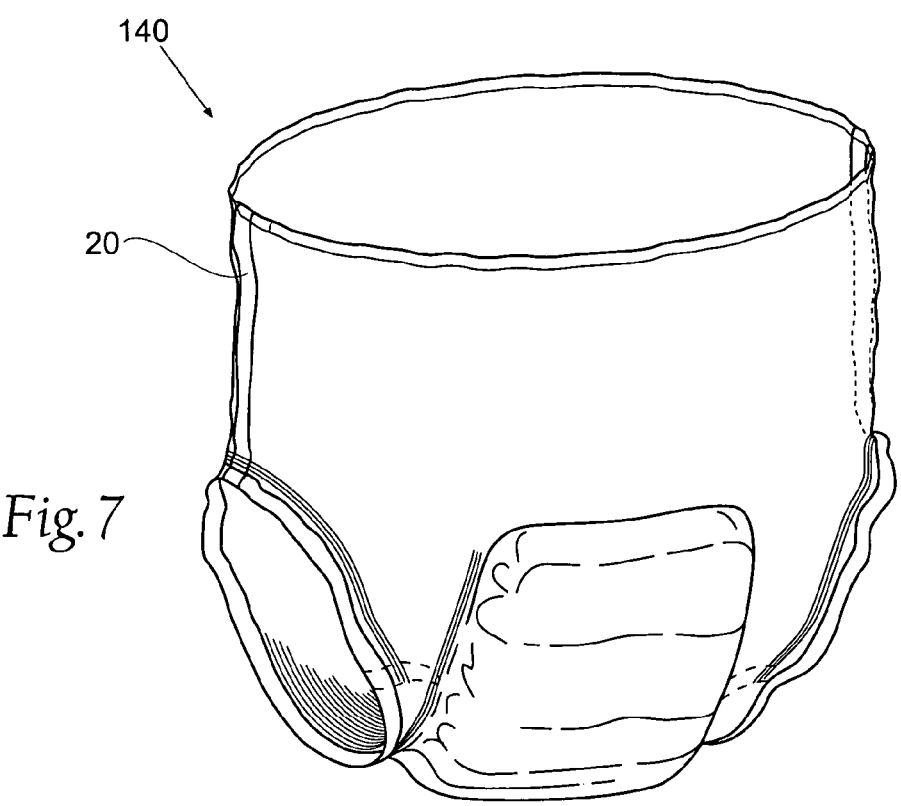
FIG. 7 is a disposable undergarment formed according to the present invention.

As shown in FIGS. 6 and 7 the resulting undergarment 140 has lap seams 20. As is evident by the fragmentary view of FIG. 6, when opposing forces F caused by normal wear of the garment 140 are applied to the seam 20, the entire lap seam 20 will counteract these forces. Previously, only the edges of the butt seam opposed such forces. Thus, the chance of the undergarment 140 splitting apart along the seams 20 is much less likely than in previous methods.

Referring again to FIG. 2B, when the blanks 40 enter the sealing device 100 (FIG. 5), there is a possibility that the three areas, the first web end 26, the second web end 28, and the first web section 25 will bond together. This is possible if there are any tears or rips in the webs or if the substrate may have not been properly placed between the first web end 26 and the second web end 28. This would result in both a lap seam and a butt seam, with the butt seam acting as a backup for the lap seam. Such a design is generally not preferred, but nevertheless could form a usable seam. Such a process has been contemplated by the present invention and would fall within the scope of the present invention.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

I claim:

1. A method of forming a seam in a disposable undergarment comprising the steps of:

providing a first web having a first end and a second end;

providing a second web having a first end and second end;

said first end of said first web overhanging said first end of said second web;

said second end of said second web overhanging said second end of said first web;

folding said overhanging first end of said first web over said first end of said second web;

folding said overhanging second end of said second web over said second end of said first web;

coupling said overhanging first end of said first web to said first end of said second web to form a first seam;

coupling said overhanging second end of said second web to said end of said first web to form a second seam.

2. The method of claim 1, said method further comprising providing a substrate layer between said first end of said first web and said first end of said second web.

3. The method of claim 2, wherein said substrate layer comprises a thermoplastic adhesive film.

4. The method of claim 1, wherein at least one of said first web and second webs are nonwoven.

5. The method of claim 1, at least one of said first and second seams forming a vertical waist seam.

6. The method of claim 1, wherein said coupling steps comprise ultrasonic bonding.

7. A method of forming a seam in a disposable undergarment comprising the steps of:
providing a blank comprising a top portion and a bottom portion with a horizontal axis dividing said first and second portions;

said bottom portion divided equally by a vertical axis, said vertical axis dividing said top portion unequally;

said top portion having a first edge and a second edge;

said bottom portion having a first edge and a second;

folding said blank along said horizontal axis;

said first edge of said bottom portion extending past said first edge of said top portion;

said second edge of said top portion extending past said second edge of said bottom portion;

folding said first edge of said bottom portion over said first edge of said top portion and coupling said first edge of said bottom portion to said first edge of said top portion in the vertical direction;

folding said second edge of said top portion over said second edge of said bottom portion and coupling said second edge of said top portion to said second edge of said bottom portion in the vertical direction.

8. The method of claim 7, the method further comprising applying a substrate material to at least one of said first edge of said bottom portion and said first edge of said top portion.

9. The method of claim 8, the method further comprising bonding said substrate material between said first edge of said bottom portion and said first edge of said top portion.

10. The method of claim 7, the method further comprising applying a substrate material to at least one of said second edge of said bottom portion and said second edge of said top portion.

11. The method of claim 10, the method further comprising bonding said substrate material between said second edge of said bottom portion and said second edge of said top portion.

* * * * *